(12) United States Patent
Morimoto

(10) Patent No.: US 11,833,020 B2
(45) Date of Patent: *Dec. 5, 2023

(54) ARRAY OF WEARABLE ARTICLES

(71) Applicant: The Procter & Gamble Company, Cincinnati, OH (US)

(72) Inventor: Koichi Morimoto, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,967

(22) Filed: Jul. 29, 2022

(65) Prior Publication Data

US 2022/0362075 A1    Nov. 17, 2022

Related U.S. Application Data

(63) Continuation of application No. 15/632,436, filed on Jun. 26, 2017, now Pat. No. 11,432,975, which is a (Continued)

(51) Int. Cl.
*A61F 13/64* (2006.01)
*A61F 13/49* (2006.01)
(Continued)

(52) U.S. Cl.
CPC ........ *A61F 13/64* (2013.01); *A61F 13/15593* (2013.01); *A61F 13/496* (2013.01); (Continued)

(58) Field of Classification Search
CPC ............... A61F 13/64; A61F 13/49011; A61F 13/496; A61F 13/49
See application file for complete search history.

(56) References Cited

U.S. PATENT DOCUMENTS 7,118,558 B2   10/2006  Wu
7,335,190 B2   2/2008   Underhill et al.
(Continued)

FOREIGN PATENT DOCUMENTS

CN   101795653 A   8/2010
JP   2002172137 A  6/2002
(Continued)

OTHER PUBLICATIONS

PCT Search Report and Written Opinion for PCT/CN2014/094888 dated Sep. 23, 2015, 8 pages.
(Continued)

*Primary Examiner* — Catharine L Anderson
*Assistant Examiner* — Arjuna P Chatrathi
(74) *Attorney, Agent, or Firm* — Charles R. Matson

(57) ABSTRACT

Disclosed is an array 1 of wearable articles 20, each article comprising a main body 38 and a ring-like elastic belt 40 comprising a front belt and a back belt wherein at least the front belt or the back belt is an elastic member having an elastic member width in the transverse direction and a non-elastic region; wherein a first elastic member of a first article comprises a first non-elastic region; a second elastic member of a second article comprises a second non-elastic region; a third elastic member of a third article comprises a third non-elastic region; wherein the elastic member width of the first, second, and third elastic members are the same; and the first, second, and third non-elastic regions are different from each other.

21 Claims, 9 Drawing Sheets

Related U.S. Application Data continuation of application No. PCT/CN2014/094888, filed on Dec. 25, 2014.

(51) Int. Cl.
  *A61F 13/496* (2006.01)
  *A61F 13/15* (2006.01)
  *A61F 13/551* (2006.01)

(52) U.S. Cl.
  CPC .............. *A61F 13/49011* (2013.01); *A61F 13/55105* (2013.01); *A61F 13/49* (2013.01)

(56) References Cited

U.S. PATENT DOCUMENTS

| | | |
|---|---|---|
| 8,092,438 B2 | 1/2012 | Betts |
| 8,382,735 B2 | 2/2013 | Torigoshi et al. |
| 8,679,296 B2 | 3/2014 | Qin et al. |
| 9,050,213 B2 | 6/2015 | Lavon |
| 9,233,031 B2 | 1/2016 | Ichihara et al. |
| 9,999,549 B2 | 6/2018 | Lavon et al. |
| 11,432,975 B2 * | 9/2022 | Morimoto ......... A61F 13/49011 |
| 2003/0135186 A1 | 7/2003 | Olson |
| 2004/0133180 A1 | 7/2004 | Mori |
| 2004/0158217 A1 | 8/2004 | Wu |
| 2006/0111686 A1 | 5/2006 | Schneider |
| 2009/0198207 A1 | 8/2009 | Torigoshi et al. |
| 2009/0266733 A1 | 10/2009 | Betts |
| 2011/0071488 A1 | 3/2011 | Kuwano et al. |
| 2011/0082435 A1 | 4/2011 | Davis |
| 2012/0152447 A1 | 6/2012 | Schneider |
| 2012/0179313 A1 | 7/2012 | Hartl et al. |
| 2012/0283683 A1 | 11/2012 | Tai et al. |
| 2013/0110068 A1 | 5/2013 | Nelson |
| 2013/0255863 A1 | 10/2013 | Lavon |
| 2013/0261589 A1 | 10/2013 | Fujkawa |
| 2013/0281954 A1 | 10/2013 | Ishihara |
| 2013/0331807 A1 | 12/2013 | Ichihara et al. |
| 2014/0378932 A1 | 12/2014 | Seitz |
| 2017/0065461 A1 | 3/2017 | Schneider |
| 2017/0290721 A1 | 10/2017 | Morimoto |
| 2020/0130910 A1 | 4/2020 | Steeves-kiss et al. |

FOREIGN PATENT DOCUMENTS

| | | |
|---|---|---|
| JP | 2004298362 | 10/2004 |
| WO | 2009155326 A1 | 12/2009 |
| WO | 2013148385 A1 | 10/2013 |

OTHER PUBLICATIONS

PCT Supplementary International Search Report or Declaration for PCT/CN2014/094888 dated Feb. 13, 2017, 10 pages.
All Office Actions; U.S. Appl. No. 15/632,436, filed Jun. 26, 2017.
Third Party Opposition filed for European Patent Application Ser. No. 14908763.7, Dated Apr. 23, 2020; 17 pages.

* cited by examiner

ARRAY OF WEARABLE ARTICLES

CROSS REFERENCE TO RELATED APPLICATIONS

This application is a continuation of U.S. application Ser. No. 15/632,436, filed on Jun. 26, 2017 which is a continuation, under 35 USC 120, of Application No. PCT/CN2014/094888, filed on Dec. 25, 2014, which are herein incorporated by reference in entirety.

FIELD OF THE INVENTION

The present invention relates to an array of wearable articles having an elastic belt which may be made in a cost effective manner.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tend to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. Belt-type pants are advantageous in that they have good breathability around the elastic belt, and in that they may be manufactured economically. The waist belts of such pants may be made by advancing two layers of continuous sheets in a machine direction, advancing and stretching a plurality of elastic bodies in the machine direction, adhering the elastic bodies between the two layers of continuous sheets wherein the portion of elastic bodies overlapping the core are left unadhered, cutting the elastic strands in regions where the elastic bodies are left unadhered, and cutting and seaming the obtained combined two sheets of continuous sheets and elastic strands in the cross-machine direction. The density, elongation, and interval of the elastic bodies may be profiled. For providing an array of such belt-type pants of different sizes, adjusting the elastic profiling is effective to some extent, however, only over similar size ranges. For providing a wide variety of sizes, the waist belt width, namely the pitch at which the assembly is cut and seamed in the cross-machine direction, may be changed. Such practice, however, requires equipment changes when a size changeover is required, and may not be effective from a capital investment and maintenance point of view.

Based on the foregoing, there is a need for providing an array of wearable articles having a variety of elastic belts in a cost effective manner There is further a need for providing such array without compromise to performance such as fit, comfort, and containment capability.

SUMMARY OF THE INVENTION

The present invention is directed to an array of wearable articles, each article continuous in a longitudinal direction and a transverse direction, comprising a main body and a ring-like elastic belt comprising a front belt and a back belt wherein at least the front belt or the back belt is an elastic member, the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, the elastic member formed by a plurality of elastic bodies running in the transverse direction sandwiched between an inner sheet and an outer sheet; each front belt and back belt having transversely continuous proximal and distal edges, the proximal edge being located closer than the distal edge relative to the longitudinal center of the article, the elastic member having an elastic member width in the transverse direction in the uncontracted condition and a non-elastic region; wherein a first elastic member of a first article comprises a first non-elastic region;

a second elastic member of a second article comprises a second non-elastic region;

a third elastic member of a third article comprises a third non-elastic region; wherein the elastic member width of the first, second, and third elastic members are the same; and the first, second, and third non-elastic regions are different from each other.

The present invention is further directed to a method of making an array of elastic members.

The present invention is further directed to a method of designing an array of articles of different size.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
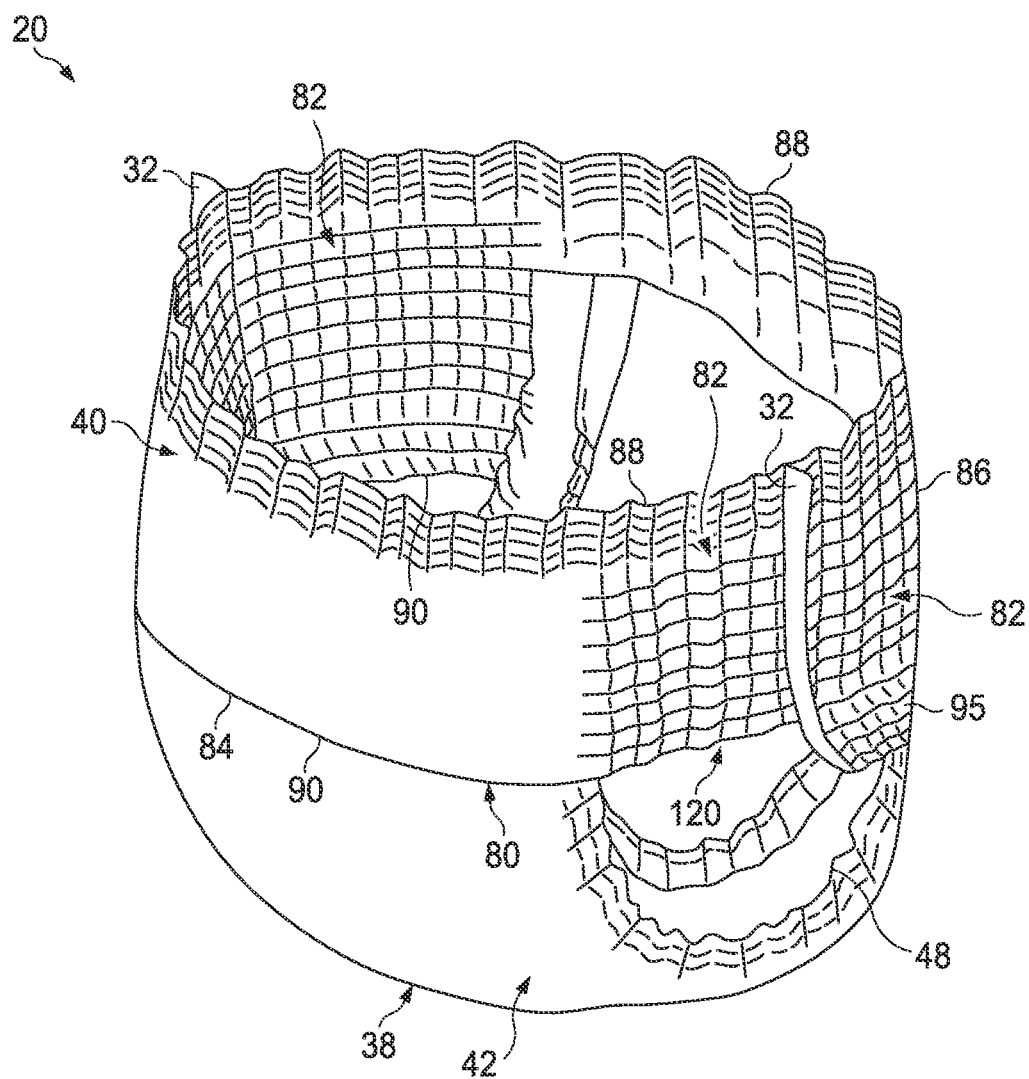
FIG. 1 is a perspective view of one embodiment of a wearable article of an array of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 2:
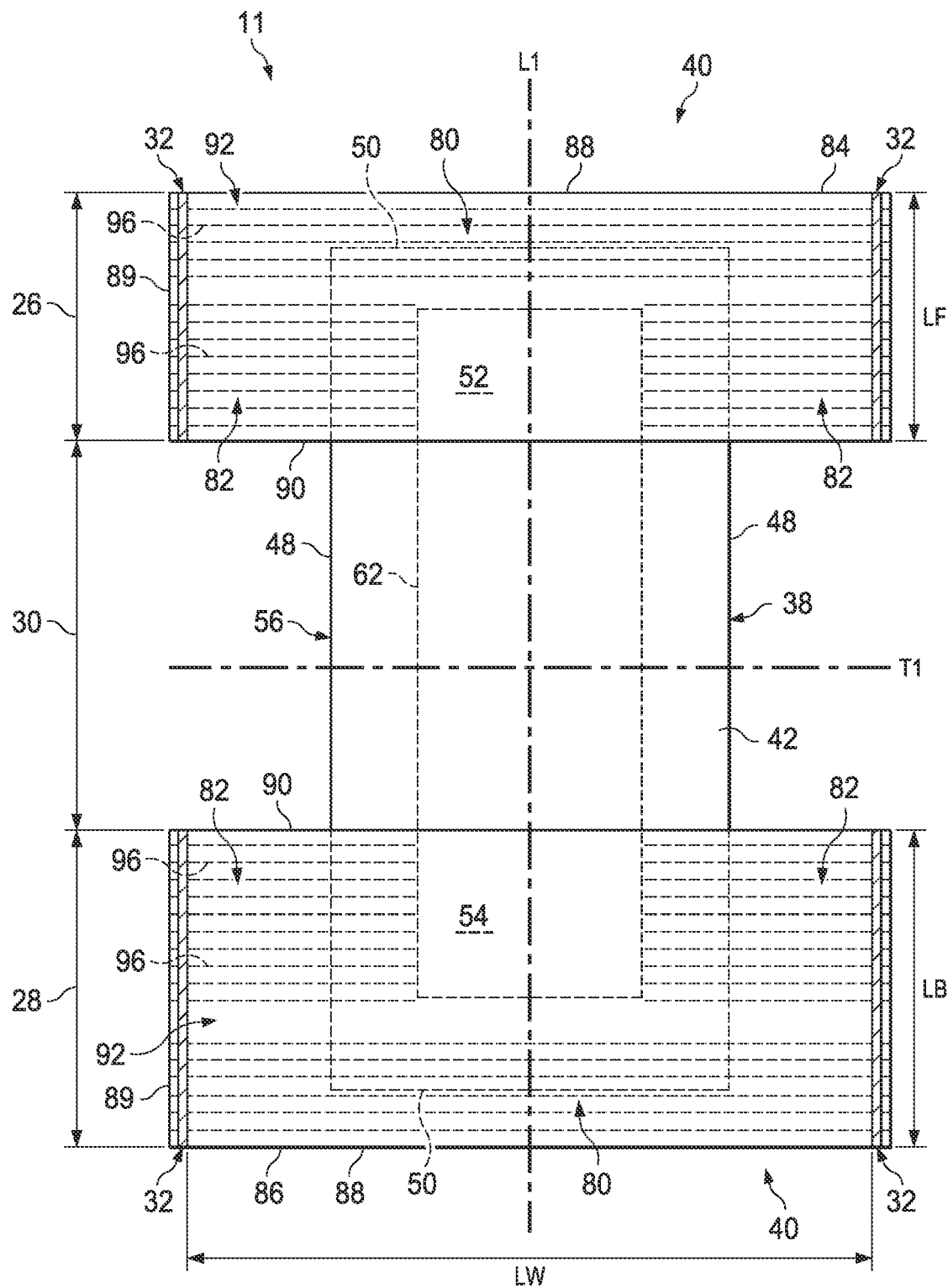
FIG. 2 is a schematic plan view of a wearable article of an array of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The articles 20 of the array of the present invention all have such basic configuration. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap.

Referring to FIGS. 1 and 2, the ring-like elastic belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, at least one of the front belt 84 and back belt 86 may be an elastic member each comprising an inner sheet 94, an outer sheet 92, (hereinafter also collectively "belt sheets") and a plurality of elastic bodies 96 sandwiched therebetween and running in the transverse direction substantially parallel to each other, and configured to impart elasticity. (The inner sheet 94 is not shown.) Such an article may be economically made.

The elastic member of the present invention has an elastic member width LW in the uncontracted condition. When the front and back belt 84, 86 are both elastic members, the elastic member width LW of the front and back belt 84, 86 may be the same. In one embodiment, each of the proximal edges 90 and the distal edges 88 of the front belt 84 and the back belt 86 may be substantially parallel, as in FIG. 2.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length. When the front belt 84 has straight distal edges 88 and proximal edges 90 that are substantially parallel of each other, then the longitudinal length LF of the front belt 84 is equal to the seam length.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in non-woven material having a basis weight of less than 45 gsm for sake of breathability perception and softness of the belt 40.

The present invention is related to providing an array of wearable articles having a variety of elastic belts in a cost effective manner. The array of articles herein may be size variations, gender variations, or any other difference in article construction that serves a diverse wearer, or a developing wearer. The array of articles may be offered as a variation or series of merchandize under the same or similar product name or any other indication for the merchandize. The array of articles of the present invention may comprise first, second, third, fourth, fifth, sixth, and seventh articles. In one embodiment, the array of the present invention is a size variation of pant-type absorbent articles for young children, the articles of the array ranging in sizes 1-6 (NB, S, M, L, XL, XXL), or a subset of at least 3 of any of such sizes. In one embodiment, the array of the present invention includes a gender variation of pant-type adult incontinence products. In one embodiment, the array of the present invention includes a containment variation of pant-type feminine protection products.

Figure 3:
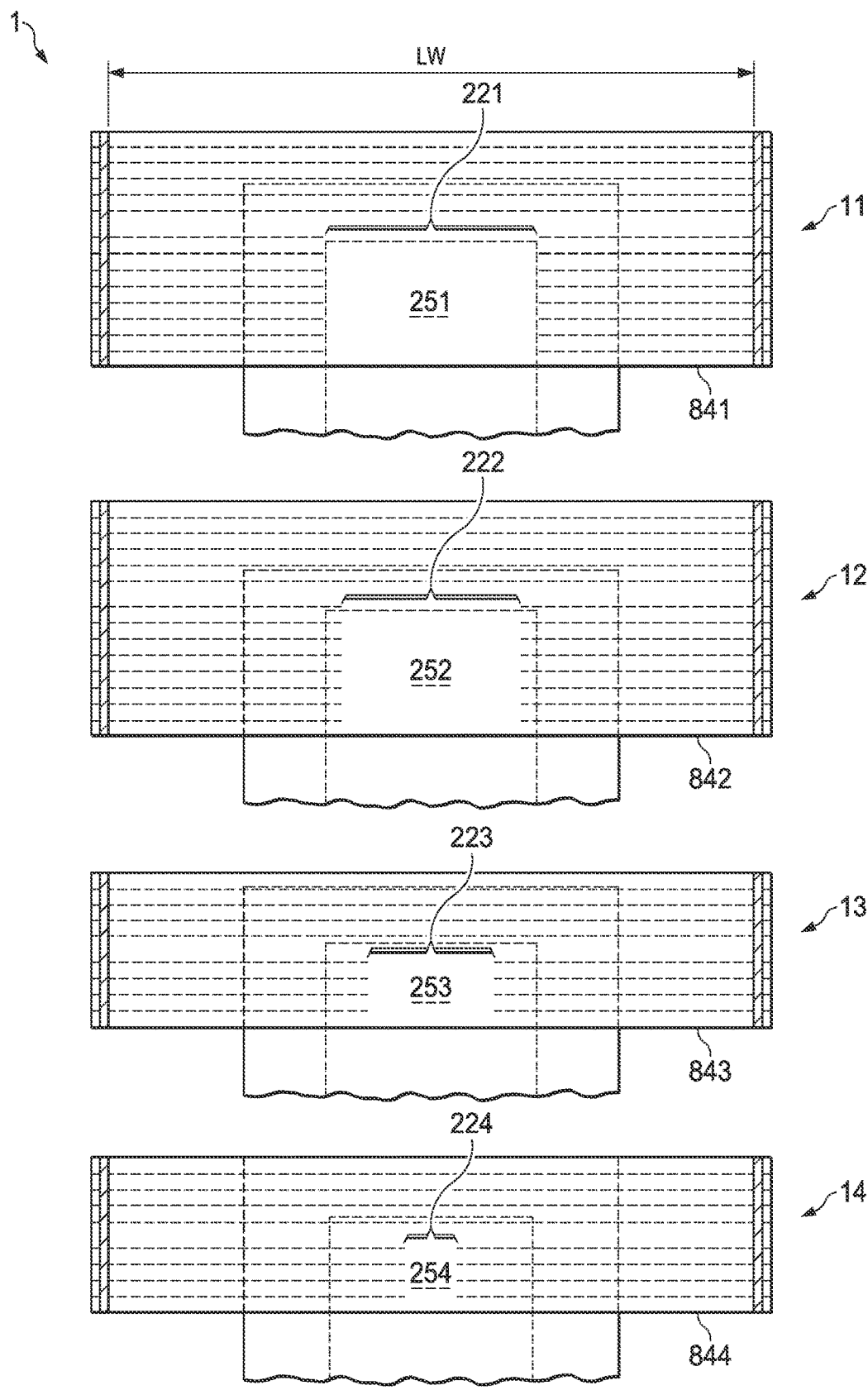
FIG. 3 is a schematic plan view of articles of an array of elastic members of the present invention.
Figure 4:
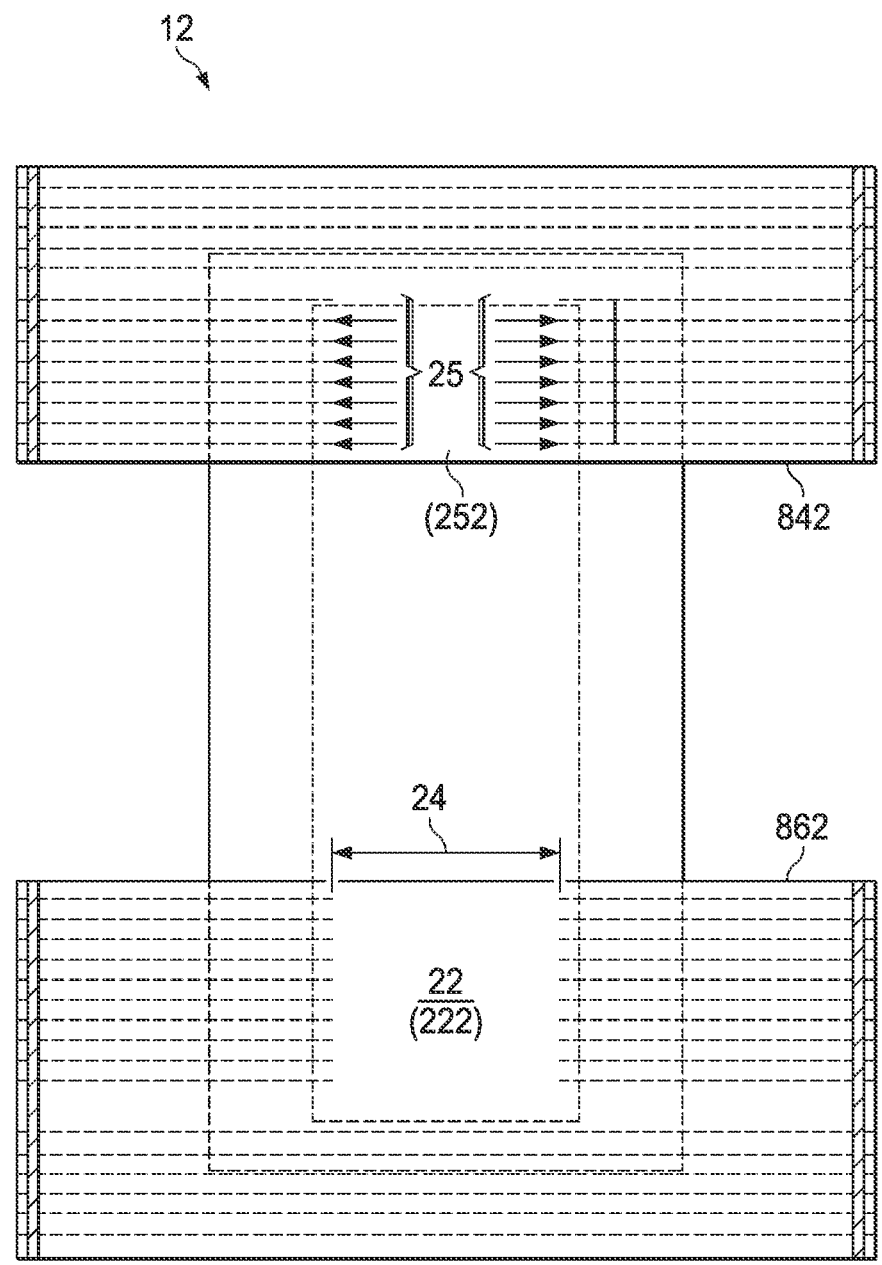
FIGS. 4-6 are schematic plan views of wearable articles of an array of the present invention with the seams unjoined and in a flat uncontracted condition showing the garment facing surface.
Figure 6:
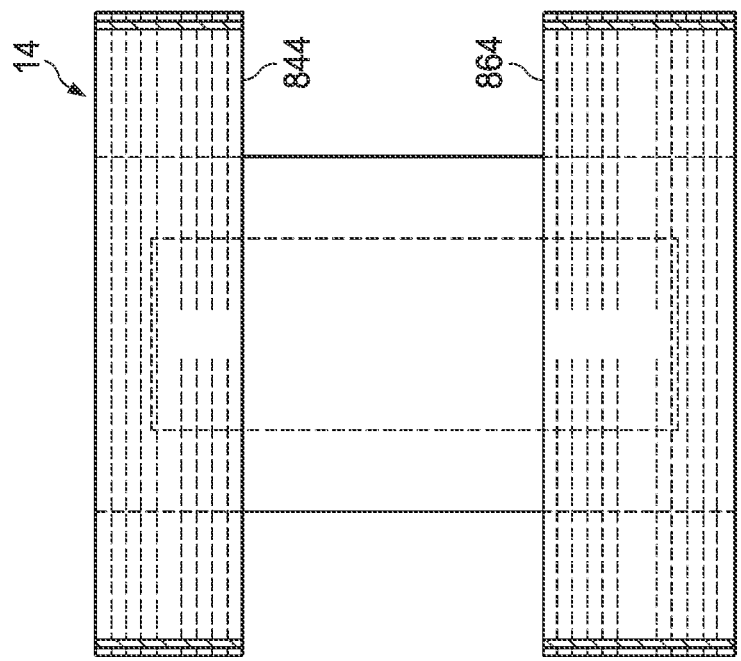
Figure 5:
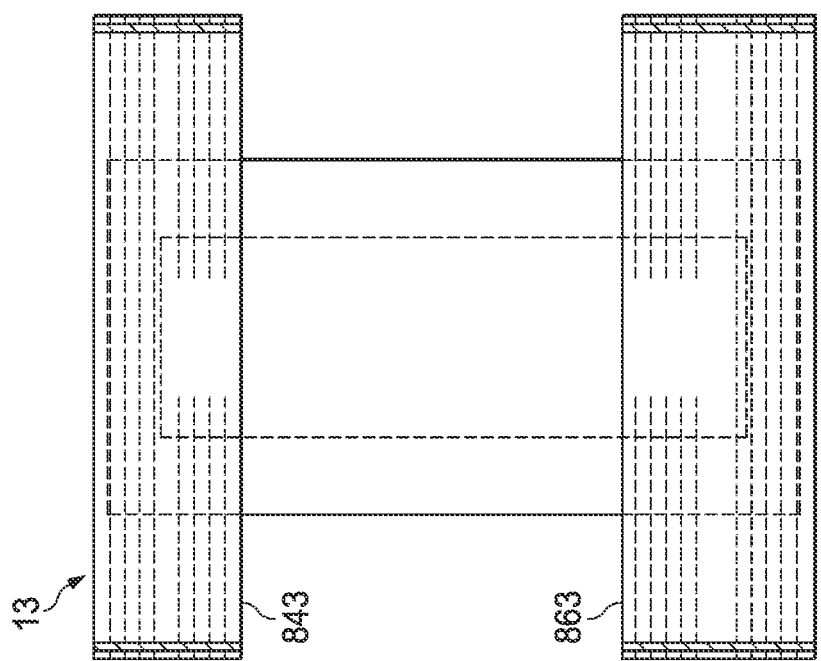
Figure 7:
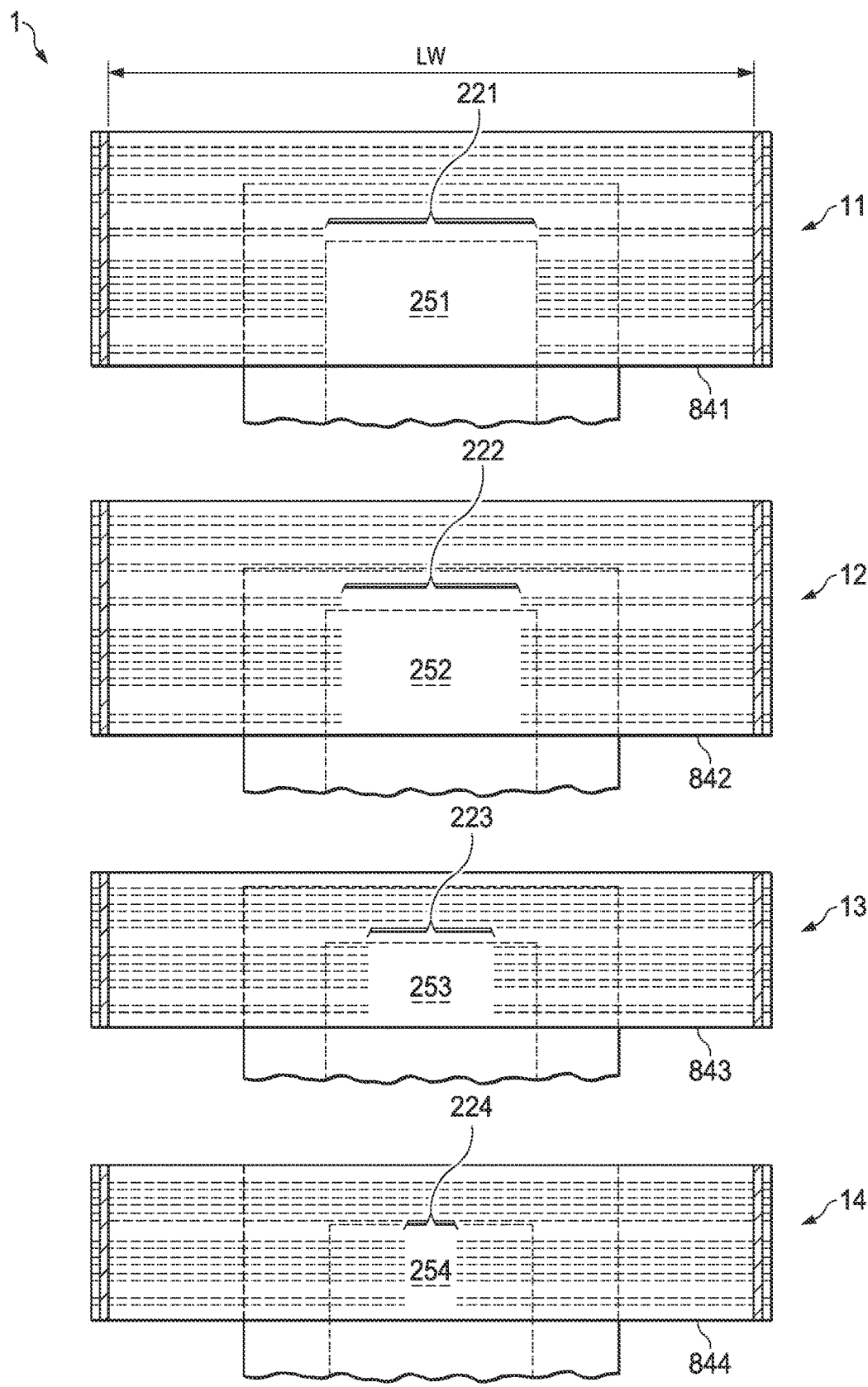
FIG. 7 is a schematic plan view of articles of an array of elastic members of the present invention.
Figure 9:
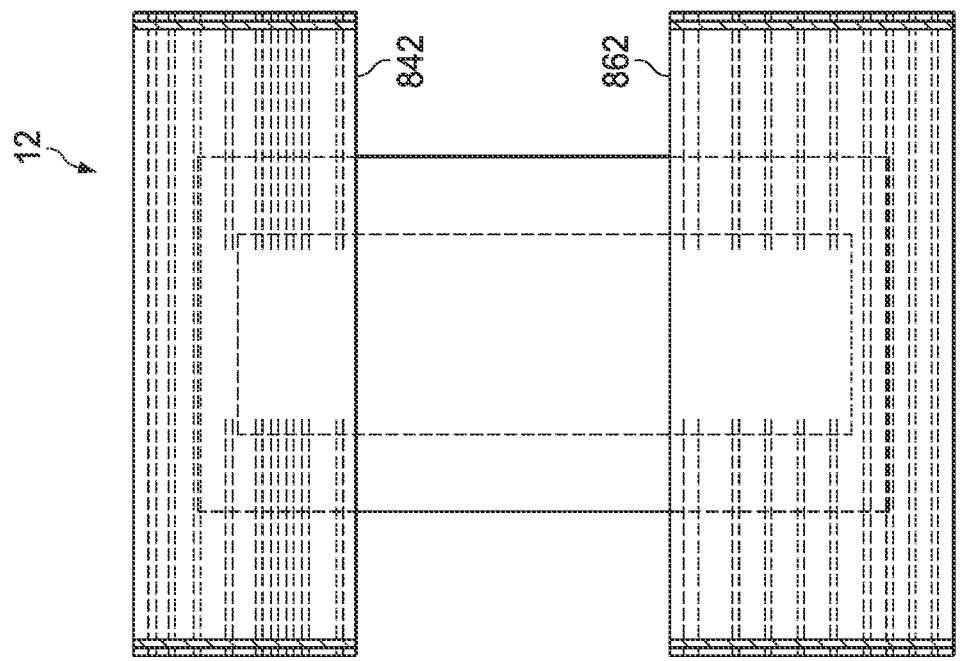
FIGS. 8-11 are schematic plan views of wearable articles of an array of the present invention with the seams unjoined and in a flat uncontracted condition showing the garment facing surface.
Figure 8:
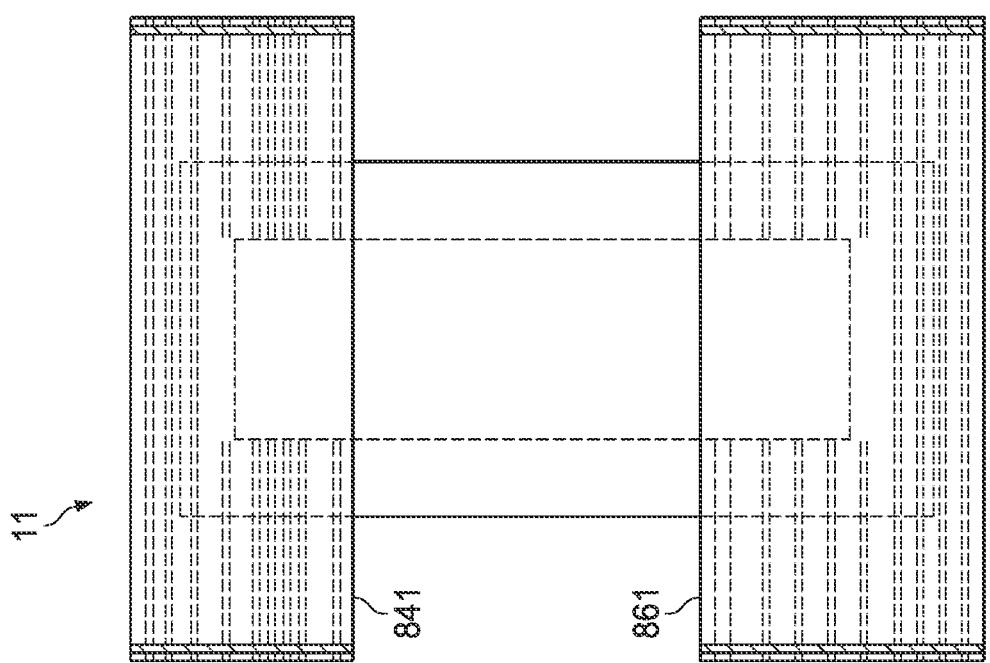
Figure 11:
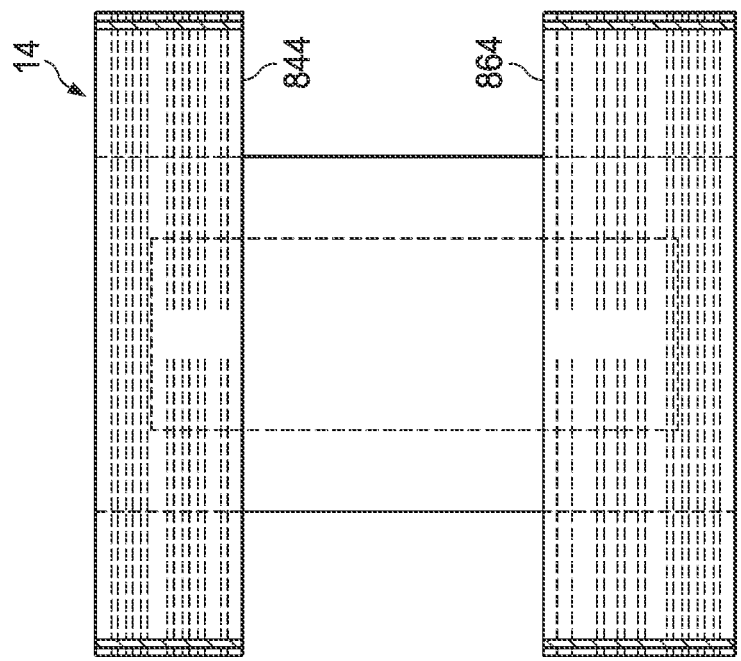
Figure 10:
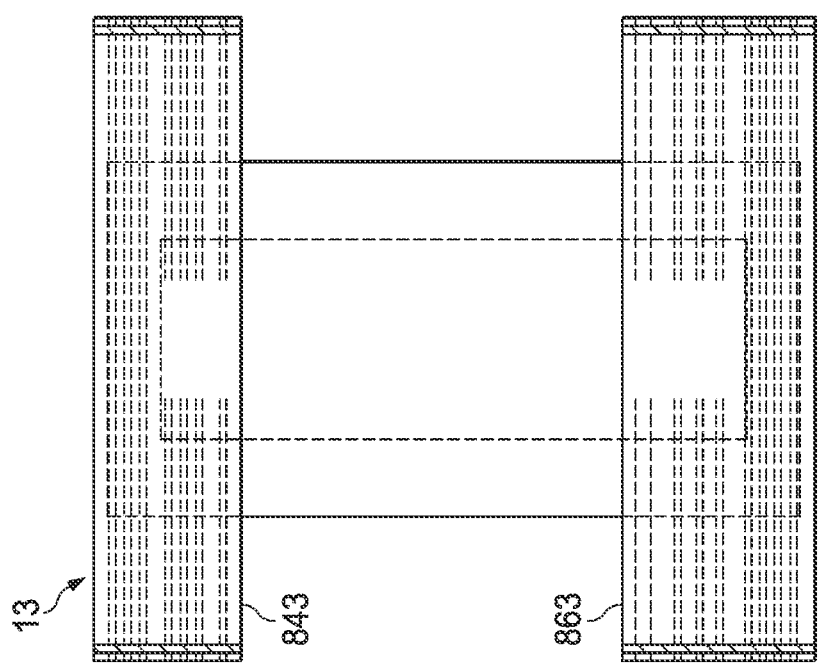

Referring to FIGS. 3 and 7, the array 1 of wearable articles herein may be a size variation of at least 3 different sizes of a pant wearable article for young children. For each array, the wearable articles herein each comprise an elastic member, wherein the elastic members all have the same elastic member width LW in the uncontracted condition, while effecting a size difference by other configurations. The elastic member may be the front belt or the back belt. Both the front belt 84 and back belt 86 may be elastic members. The elastic member width LW of the front and back belt 84, 86 may be matched. Such commonality of elastic member width LW over the entire array 1 of articles provides significant manufacturing efficiency from a capital investment and maintenance point of view. Moreover, despite such commonality, each article may be provided without compromise to performance such as fit and containment capability. The other configurations that may effect a size difference within the array include, for example, elastic member length (LB, LF), and profiling of the elastic bodies disposed on the elastic member.

The tensile stress (N/m) of the elastic member correlates to the degree of contraction of the elastic member when worn. Therefore, by controlling the tensile stress of the elastic member per article, each article may be provided to meet a particular size specification, even when having the same belt width (LW). The tensile stress of elastic bodies within the elastic member may also be profiled in order to provide good fit and containment capability for the article of a particular size, taking into consideration not only the size, but developmental factors such as change in body proportion and mobility. The elasticity of the elastic member is provided by a plurality of elastic bodies 96 running in the transverse direction, the tensile stress adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body.

Each elastic body 96 disposed on the elastic member may be disposed over the entire transverse width LW of the elastic member. Some elastic bodies 96 may not be disposed in the transverse center of the elastic member, or removed of its elasticity contributing to the elasticity of the elastic member in the transverse center. When a portion of an elastic body is not contributing to the elastic member, the remainder of the intact elastic body capable of imparting elasticity to the elastic member is defined as the "effective length of elasticity of an elastic body". An elastic body unadhered to the sheets constructing the elastic member may be left dangling, thereby still exhibiting elasticity as an elastic body per se. However, so long as the elasticity is non-contributory to elasticity of the elastic member, such length or area is described herein as "non-elastic". The accumulative area of the elastic member in the transverse center where elasticity of the elastic body 96 is absent is herein defined as the non-elastic region 22.

In one embodiment, the elastic member of the present invention may be made by the steps of:
(a) advancing two layers of continuous sheets, for example the inner and outer sheets 92 94, in a machine direction;
(b) advancing and stretching a plurality of elastic bodies 96 in the machine direction;
(c) adhering the elastic bodies 96 between the two layers of continuous sheets wherein at least a certain portion of some of the elastic bodies are left unadhered, the unadhered portion being an elastic cut window 24;
(d) cutting the elastic strands at the elastic cut windows 24; and
(e) cutting and seaming the obtained assembly of step (d) in the cross-machine direction to define an elastic member width LW.

In this embodiment of making the elastic member, the set of elastic cut windows 25 defines the non-elastic region 22. Such an elastic member may be economically made.

Referring again to FIGS. 2-11, the array 1 of wearable articles of the present invention comprises at least first, second, and third articles 11, 12, 13, wherein at least the front belt 84 or the back belt 86 of each article is an elastic member, wherein a first elastic member of a first article 11 comprises a first non-elastic region 221; a second elastic member of a second article 12 comprises a second non-elastic region 222; a third elastic member of a third article 13 comprises a third non-elastic region 223; wherein the elastic member width LW of the first, second, and third elastic members are the same, and the first non-elastic region 221 and second non-elastic region 222 and third non-elastic region 223 are different from each other. The array of articles of the present invention may further comprise a fourth elastic member of a fourth article 14 comprising a fourth non-elastic region 224, as in the embodiments of FIGS. 3 and 7. The array of articles of the present invention may further comprise a fifth elastic member of a fifth article 15 comprising a fifth non-elastic region 225, a sixth elastic member of a sixth article 16 comprising a sixth non-elastic region 226, and a seventh elastic member of a seventh article 17 comprising a seventh non-elastic region 227.

For providing such different non elastic regions 22, a first elastic member of a first article 11 may comprise a first set of elastic cut windows 251; a second elastic member of a second article 12 may comprise a second set of elastic cut windows 252; a third elastic member of a third article 13 may comprise a third set of elastic cut windows 253; wherein the first set of elastic cut windows 251, second set of elastic cut windows 252, and third set of elastic cut windows 253 are different from each other.

In one embodiment, the front belt and back belt of each article of the present array are elastic members, the first article 11 comprising a first front elastic member which is the first front belt 841 and a first back elastic member which is the first back belt 861, the second article 12 comprising a second front elastic member which is the second front belt 842 and a second back elastic member which is the second back belt 862, the third article 13 comprising a third front elastic member which is the third front belt 843 and a third back elastic member which is the third back belt 863, and so forth. For each article, the non-elastic region 22 of the front belt 84 and back belt 86 of each article may be different. For each article, the set of elastic cut windows 24 between the front belt 84 and back belt 86 may be the same or different.

Referring again to FIGS. 2-11, in one embodiment, the array of the present invention may provide a size variation of pant-type absorbent articles in sizes 1-4 (NB, S, M, L). Such array may include articles having a length along the longitudinal axis in the range of from 350 mm to 570 mm, or from 370 mm to 480 mm. The first article 11 comprises a first elastic element for forming a first front belt 841 having a first non-elastic region 221 made by a first set of elastic cut windows 251. Similarly, the second article 12 comprises a second elastic element for forming a second front belt 842 having a second non-elastic region 222 made by a second set of elastic cut windows 252. The first set of elastic cut windows 251 is larger than the second set of elastic cut windows 252, resulting in the first non-elastic region 221 being larger than the second non-elastic region 222. The second set of elastic cut windows 252 is larger than the third set of elastic cut windows 253, the third set of elastic cut windows 253 is larger than the fourth set of elastic cut windows 254. The elastic cut windows 24 per elastic member may be all the same, resulting in non-elastic regions 22 of the articles having a substantially rectangular shape as shown in FIGS. 2-11. Alternatively, the elastic cut windows 24 per elastic member may be profiled such that the non-elastic region is not rectangular. In one embodiment, the article of the smallest size may have virtually no elastic cut window 24, namely, have all elastic bodies disposed on the elastic member having complete elasticity over the elastic member width LW. Even in such embodiment, the "zero elastic cut window" will be considered a set of elastic cut windows 25.

By providing the array with such configurations, each elastic member of the array may be configured to provide different contraction levels, the elastic members with smaller elastic cut windows having higher contraction levels. As such, the resulting elastic member in the contracted condition may be configured to provide different sizes of elastic belts 40 per article 20, such that a size variation is actualized. Each article of the present invention has an Initial Gauge Circumference and a Full Stretch Circumference according to the Whole Article Force Measurement described herein below. In one embodiment, each article of the array 1 is so configured such that the percentage of the Initial Gauge Circumference to the Full Stretch Circumference of the elastic belt 40 is from 28% to 40%, or from 30% to 38%. When the articles 20 of an array 1 have the same belt width LW and the same longitudinal length of the belt (LB, LF), the Full Stretch Circumference of the articles 20 within an array 1 will be identical. When the articles 20 of an array 1 have the same belt width LW and different longitudinal length of the belt (LB, LF), the Full Stretch Circumference of the articles 20 within an array 1 will be approximately the same with a deviation of less than 10%, or less than 6%, depending on the elastic profile of the elastic member.

Without being bound by theory, by configuring the elastic belts 40 of an array 1 to the percentage of the Initial Gauge Circumference to the Full stretch circumference within the aforementioned range, an article having good fit and comfort to the wearer of each size may be obtained. Conversely, a method of designing an array of articles of different size, each having good fit and comfort, may be provided by configuring each article to have a percentage of the Initial Gauge Circumference to the Full stretch circumference is from 28% to 40%, or from 30% to 38%.

In addition to adjusting the set of elastic cut windows 25, the elongation rate of the elastic body 96, density (dtex) of the elastic body 96, and longitudinal interval of multiple elastic bodies 96 may be adjusted to actualize size variation. Further, the overall elastic profiling of the front and/or back belt may be changed per size, for conforming to the different body shapes of the lower torso of a developing young child. For example, a larger size article may be configured to have an anchoring system that provides high tensile stress at the area of the trochanter bone of the front belt for fit of active large babies. In another example, a smaller size article may be configured to have a belt with uniform low tensile stress for comfort of less mobile small babies.

The main body 38 may contain an absorbent core 62 for absorbing and containing body exudates disposed on the main body 38, the absorbent core 62 overlapping at least a portion of the front belt 84 and the back belt 86. In this embodiment, the non-elastic region 22 of each article may overlap the absorbent core 62. Removal of elasticity from at least a portion of the area overlapping the absorbent core 62 may be advantageous, in that elasticity in the front and/or back area may cause bunching of the absorbent core 62 and interfere with close fit of the main body 38 to the wearer. Depending on the size of the article, at least 10% of, or at least 20% of, or at least 30% of, the elasticity of; at least one of, or at least half of, or at least two thirds of, or all of, the elastic bodies are removed in the region overlapping with the absorbent core 62 of the main body 38. For smaller sizes having smaller non-elastic regions 22, there may be areas left overlapping with the absorbent core 62. At least one elastic member of at least one article may have a non-elastic region 22 having a transverse width which is shorter than the transverse width of the absorbent core 62, such as the third front belt 84₃, the fourth front belt 84₄, the third back belt 86₃, and the fourth back belt 96₄, in FIGS. 5, 6, 10, and 11.

In one embodiment, an elastic cut window 24 may be formed at regions where the absorbent core 62 does not overlap with the front or back belt 84, 86. Such configuration may be advantageous for providing a large non-elastic region 22 extending in the transverse direction from the absorbent core 62 for making articles of larger sizes. In another embodiment, an elastic cut window 24 may be formed on the front belt 84 distal from the absorbent core, to provide a front belt which is more extendable toward the waist opening to accommodate the relatively big belly of a small baby.

In one embodiment, the elongation of the elastic bodies 96 disposed on the front and back belt 84, 86 of the same distance from the distal edge may be substantially matched. When a certain length of the elastic body is removed of its elasticity, the effective length of elasticity of such elastic body is considered. By matching the elongation rate of the elastic bodies disposed on the front and back of the same distance from the distal edge, and having the front and back belt 84, 86 have the same width LW, the article 20 may be manufactured such that in the unstretched, contracted condition, the article 20 can be flattened. Such flattening capability is found for many commercially available pant-type wearable articles, and provides many benefits for providing the article economically. In one embodiment, such matched elongation rate may further be matched between multiple articles in the array, or over the entire array. The capability of being flattened accommodates assembling, transferring, and packaging of the article 20, and particularly so, for multiple or all articles of an array.

The article of the present invention may be made with a total of no more than 60, or no more than 46 elastic bodies for the elastic belt 40 per article. The article of the present invention may have a Waist Circumference Force provided by the elastic bodies 96 disposed on the waist belt 40 of no more than 10 N, or no more than 8 N, according to the Whole Article Force Measurement. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6 N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 12:
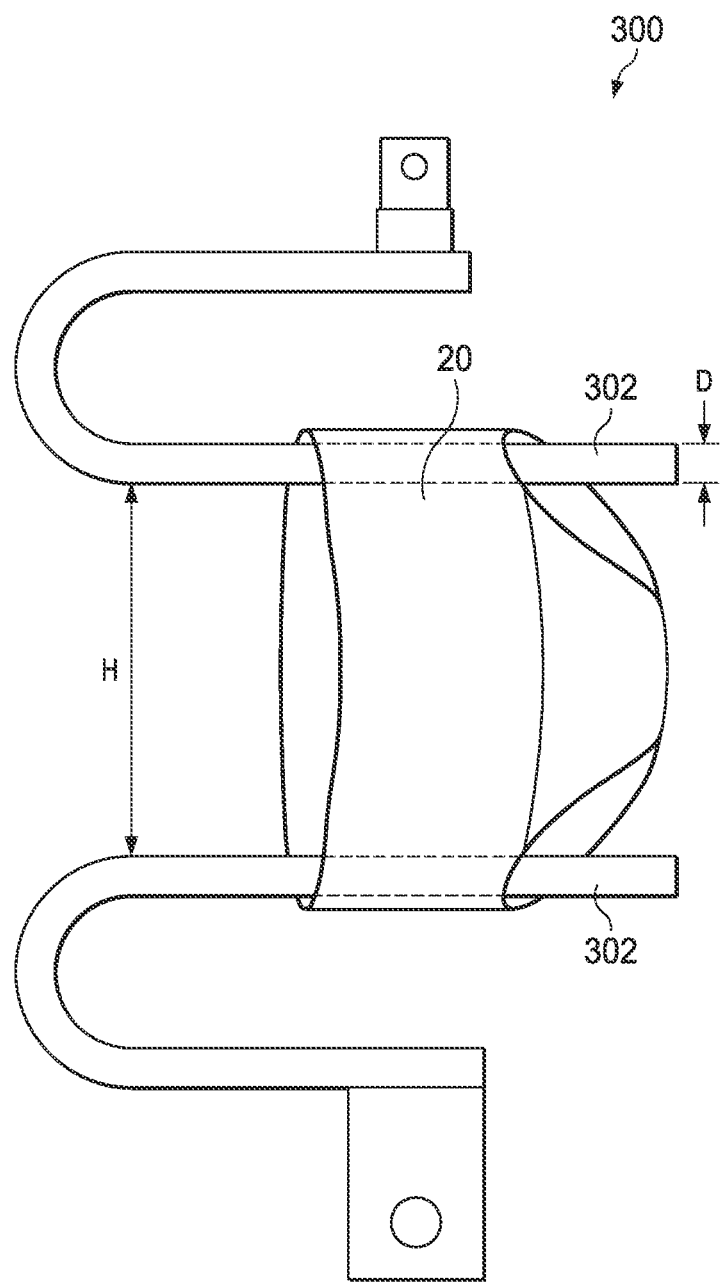
FIG. 12 is a schematic view of an example of a hanger-type sample holding fixture according to the "Whole Article Force Measurement".

The tensile tester is fitted with hanger-type sample holding fixtures 300 as shown in FIG. 12. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| Crosshead Speed | 254.0 mm/min |
|---|---|
| Final Load Point | 19.61 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1 N, while taking care not to add any unnecessary force. The gauge circumference at this point is the Initial Gauge Circumference. The test is initiated and the crosshead moves up at 254 mm/min until a force of 19.6 N is attained, then the crosshead immediately returns to the initial gauge circumference at the same speed. The maximum circumference at 19.6 N and the force at 70% stretch circumference during the extension segment of the test are recorded.

Circumference (mm)=2×(H+D+πD/2)

The maximum circumference at 19.6 N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

EXAMPLES

Example 1

An array of wearable articles of the present invention having an elastic profiling according to FIGS. 2 and 4-6, and dimensions of Table 2 below.

TABLE 2

| Figure | 6 | 5 | 4 | 2 |
|---|---|---|---|---|
| Size | NB (1) | S (2) | M (3) | L (4) |
| LW | 355 mm | 355 mm | 355 mm | 355 mm |
| LF | 85 mm | 85 mm | 121 mm | 121 mm |
| LB | 111 mm | 111 mm | 156 mm | 156 mm |
| Front belt elastics distal side (dtex/prestretch %/# of elastics) | 940 dtex/ 275%/4 | 940 dtex/ 232%/4 | 940 dtex/ 210%/4 | 940 dtex/ 210%/4 |
| Front belt elastics proximal side with elastic cut window (dtex/prestretch %/# of elastics) | 680 dtex/ 275%/4 | 680 dtex/ 275%/4 | 680 dtex/ 275%/8 | 680 dtex/ 275%/8 |
| Back belt elastics distal side (dtex/prestretch %/# of elastics) | 940 dtex/ 275%/2 | 940 dtex/ 232%/2 | 940 dtex/ 210%/2 | 940 dtex/ 210%/2 |
| | 1100 dtex/ 275%/2 | 1100 dtex/ 230%/2 | 1100 dtex/ 170%/3 | 1100 dtex/ 170%/3 |
| Back belt elastics proximal side with elastic cut window (dtex/prestretch %/# of elastics) | 680 dtex/ 275%/3 | 680 dtex/ 275%/3 | 680 dtex/ 275%/7 | 680 dtex/ 275%/7 |
| Back belt elastics buttock cover with elastic cut window (dtex/prestretch %/# of elastics) | 680 dtex/ 232%/1 | 680 dtex/ 232%/1 | 680 dtex/ 232%/2 | 680 dtex/ 232%/2 |
| | 1100 dtex/ 232%/1 | 1100 dtex/ 232%/1 | 1100 dtex/ 232%/1 | 1100 dtex/ 232%/1 |
| Elastic cut window | 30 mm | 70 mm | 100 mm | 120 mm |
| Initial Gauge Circumference (IGC) | 201 mm | 227 mm | 245 mm | 245 mm |
| Full Stretch Circumference (FSC) | 681 mm | 681 mm | 644 mm | 644 mm |
| IGC/FSC | 30% | 33% | 38% | 38% |

Example 2

An array of wearable articles of the present invention having an elastic profiling according to FIGS. 8-11, and the following dimensions being the same as Example 1: LW, LF, LB, prestretch of elastics, and elastic cut window.

The array of articles of Examples 1 and 2, respectively, are made with front and back belts, respectively of the same belt width LW over all articles, and provides appropriate fit for each size. The array of articles of Examples 1 and 2 are made economically, as there is less time required for size turnover. Each article of the array of Examples 1 and 2 has good fit, comfort, and containment capacity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of wearable articles, each article continuous in a longitudinal direction and a transverse direction, comprising a main body and a ring-like elastic belt comprising a front belt and a back belt wherein at least the front belt or the back belt is an elastic member,
the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings,
the elastic member formed by at least one elastic body running in the transverse direction sandwiched between an inner sheet and an outer sheet; each front belt and back belt having transversely continuous proximal and distal edges, the proximal edge being located closer than the distal edge relative to the longitudinal center of the article,
the elastic member comprising an elastic member width defined by a width of the inner and outer sheets in the transverse direction in the uncontracted condition, and the elastic member further comprising a non-elastic region; wherein
a first elastic member of a first article comprises a first non-elastic region;
a second elastic member of a second article comprises a second non-elastic region; wherein
the elastic member width of the first and second elastic members are the same; and
the first non-elastic region is larger than the second non-elastic region;
wherein the first and second are size variations wherein a first article size is larger than a second article size.

2. The array of claim 1, wherein the at least one elastic body comprises a plurality of elastic bodies, and wherein the non-elastic region is made by the steps of a) adhering the elastic bodies between the inner sheet and outer sheet wherein at least a certain portion of some of the elastic bodies are left unadhered, the unadhered portion being an elastic cut window; and b) cutting the elastic bodies at the elastic cut windows; wherein
the first elastic member of the first article comprises a first set of elastic cut windows;
the second elastic member of the second article comprises a second set of elastic cut windows; wherein the first and second sets of elastic cut windows are different from each other.

3. The array of claim 2, wherein the front belt and the back belt of each article are elastic members,
the first article comprising a first front elastic member which is the first front belt and a first back elastic member which is the first back belt, and
the second article comprising a second front elastic member which is the second front belt and a second back elastic member which is the second back belt.

4. The array of claim 3, wherein the set of elastic cut windows of the front belt and back belt of each article is different.

5. The array of claim 3, wherein the set of elastic cut windows of the front belt and back belt of each article is the same.

6. The array of claim 1 wherein the length of the articles along the longitudinal axis are in the range of from 350 mm to 570 mm.

7. The array of claim 1, wherein each article has an Initial Gauge Circumference and a Full Stretch Circumference according to the Whole Article Force Measurement herein, wherein each article of the array is configured such that the percentage of the Initial Gauge Circumference to the Full Stretch Circumference of the ring-like elastic belt is from 28% to 40%.

8. The array of claim 1, comprising a third article comprising a third elastic member comprising a third non-elastic region.

9. The array of claim 2, wherein the main body of each article comprises an absorbent core, the absorbent core overlapping at least a portion of the front belt and the back belt.

10. The array of claim 9, wherein the set of elastic cut windows of each article overlaps the absorbent core.

11. The array of claim 10, wherein at least one elastic member of at least one article has a set of elastic windows having a transverse width which is shorter than the transverse width of the absorbent core.

12. The array of claim 9, comprising at least one article having an elastic cut window formed at regions where the absorbent core does not overlap.

13. The array of claim 12, wherein the elastic cut window is formed on the front belt longitudinally distal from the absorbent core.

14. The of array of claim 3, wherein the at least one elastic body comprise a plurality of elastic bodies, and wherein the elongation of the elastic bodies disposed on the front belt and the back belt of the same distance from the distal edge are substantially matched.

15. The array of claim 1, wherein the at least one elastic body comprise a plurality of elastic bodies, and wherein any article is disposed of a total of no more than 60 elastic bodies.

16. The array of claim 1, wherein the Waist Circumference Force according to the Whole Article Force Measurement herein of any article is no more than 10 N.

17. The array of claim 1, wherein, for any article, each of the proximal edges and the distal edges of the front belt and the back belt are substantially parallel, the longitudinal length of the back belt being longer than that of the front belt, wherein the distal edge of the front belt is aligned with the distal edge of the back belt, and the proximal edge of the front belt is not aligned with the proximal edge of the back belt.

18. The array of claim 1, wherein the elastic members of at least two of the first and second absorbent articles comprises: a same number of elastic strands.

19. The array of claim 18, wherein the elastic strands comprise an identical dtex.

20. The array of claim 19, wherein the elastic strands comprise an identical prestretch.

21. The array of claim 1, wherein the elastic members of all of the first and second absorbent articles comprises elastic strands comprising an identical dtex.

\* \* \* \* \*